United States Patent [19]

Schwarze et al.

[11] Patent Number: 4,482,759

[45] Date of Patent: Nov. 13, 1984

[54] FUNGICIDALLY ACTIVE BENZHYDROL DERIVATIVES

[75] Inventors: Werner Schwarze, Frankfurt; Axel Kleemann, Hanau, both of Fed. Rep. of Germany

[73] Assignee: Degussa Aktiengesellschaft, Frankfurt, Fed. Rep. of Germany

[21] Appl. No.: 468,593

[22] Filed: Feb. 22, 1983

[30] Foreign Application Priority Data

Feb. 20, 1982 [DE] Fed. Rep. of Germany ....... 3206225

[51] Int. Cl.³ .............................................. C07C 33/34
[52] U.S. Cl. .................................................... 568/809
[58] Field of Search ......................................... 568/809

[56] References Cited

U.S. PATENT DOCUMENTS

| 2,881,111 | 4/1959 | Craig et al. | 568/809 |
| 3,287,213 | 11/1966 | Busschots | 568/809 |
| 3,506,682 | 4/1970 | Fried | 568/809 |

FOREIGN PATENT DOCUMENTS

| 2506598 | 8/1975 | Fed. Rep. of Germany | 568/809 |
| 3206225 | 9/1983 | Fed. Rep. of Germany | 568/809 |
| 625822 | 7/1949 | United Kingdom | 568/809 |
| 831421 | 3/1960 | United Kingdom | 568/809 |

OTHER PUBLICATIONS

Cannon et al., "J. Amer. Chem. Soc." vol. 81, pp. 1660–1666 (1959).
Biro, Helvetical Chimica Acta, vol. 37, pp. 2230–2251 Dec. 1, 1954.
Bauer, Chemische Berichte, vol. 109, pp. 2186–2196 (1976).
Schwarze et al., "Chemical Abstracts" vol. 100(1983) p. 85,385k.

Primary Examiner—Werren B. Lone
Attorney, Agent, or Firm—Cushman, Darby & Cushman

[57] ABSTRACT

There are prepared compounds of the general formula

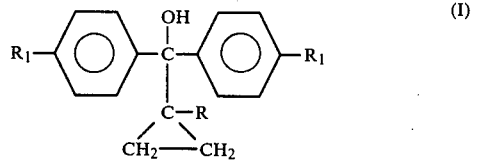

where R is methyl or ethyl and $R_1$ is halogen or hydrogen. The compounds are useful as fungicides, especially against *Piricularia oryzae* on rice.

15 Claims, No Drawings

FUNGICIDALLY ACTIVE BENZHYDROL DERIVATIVES

BACKGROUND OF THE INVENTION

The invention is directed to new benzhydrol derivatives which are distinguished by fungicidal activity, especially against *Piricularia oryzae* in rice, a process for the production of these compounds, agents containing these compounds as active material, as well as the use of these active materials as a fungicidal agent in the protection of plants.

It is known that di-(p-chlorophenyl)-cyclopropylmethanol has fungicidal activity against *Fusarium culmorum, Alternaria Tenuis, Botrytis cianera,* and *Phytophthora infestans.* Basschots, U.S. Pat. No. 3,287,213, the entire disclosure of which is hereby incorporated by reference. However, in using this active material frequently the cultivated plants are influenced disadvantageously.

It has now been found that benzhydrol derivatives of general formula (I):

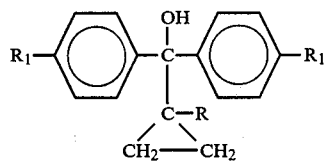

in which R is an ethyl or more preferably a methyl group and $R_1$ is a halogen or hydrogen atom exhibit an excellent fungicidal activity for the protection of cultivated plants, especially against *Piricularia oryzae* in rice, without influencing the useful plants disadvantageously through undesirable side effects.

With the active compounds of formula (I) the fungi present on plants and plant parts (fruits, blossoms, foliage, stems, tubers, roots) and related useful cultivated materials are checked or destroyed, in which case even later growing plant parts remain protected from this type of fungi.

The compounds of formula (I) furthermore can be used as a caustic agent for treating seeds (fruits, tubers, grains) and plant cuttings for protection before fungal infections as well as against phytopathogenic fungi occurring in the soil.

Especially outstanding are compounds of general formula (I) in which $R_1$ is a fluorine or chlorine and R is the methyl group. However, the preferred compound is α-(1-methyl-cyclopropyl)-4,4′-dichlorobenzhydrol.

Other compounds within formula (I) include
α-(1-methylcyclopropyl)-4,4′-difluorobenzhydrol,
α-(1-methylcyclopropyl)-4,4′-dibromobenzhydrol,
α-(1-ethylcyclopropyl-4,4′-dichlorobenzhydrol,
α-(1-ethylcyclopropyl)-4,4′-dibromobenzhydrol,
α-(1-ethylcyclopropyl)-4,4′-difluorobenzhydrol,
α-(1-methylcyclopropyl)-benzhydrol, and
α-(1-ethylcyclopropyl)-benzhydrol.

The compounds of the invention can be made from the corresponding halobenzenes or dihalobenzenes and the 1-methyl or 1-ethylcyclopropane-carboxylic acid esters in a known manner by means of a Grignard reaction.

The cyclopropylcarboxylic acid ester starting materials mentioned can be prepared according to the method described in Cannon et al, J. Amer. Chem. Soc. Vol. 81 pages 1660–1666, the entire disclosure of which is hereby incorporated by reference and relied upon.

Unless otherwise indicated all parts and percentages are by weight.

The compositions can comprise, consist essentially of or consist of the stated materials and the processes can comprise, consist essentially of the stated steps with such materials.

The following examples illustrate the invention without limiting it.

DETAILED DESCRIPTION

EXAMPLE 1

There are placed under nitrogen in a 6 liter three neck round bottom flask provided with a stirrer, a gas inlet tube, reflux condenser, inflow funnel and thermometer 192 grams of magnesium shavings.

There is prepared a solution of 1176 grams of 1,4-dichlorobenzene in 2.5 liters of tetrahydrofuran. About 200 ml of this solution were added to the magnesium shavings. There were added thereto 10 ml of ethyl bromide under stirring. After several minutes the reaction started. The remainder of the dichlorobenzene solution was then added in such manner that the mixture boiled continuously. The mixture was heated subsequently for 2 hours.

To the Grignard solution obtained there were dropped in under reflux 533.5 grams of 1-methylcyclopropane carboxylic acid ethyl ester (ethyl 1-methylcyclopropylcarboxylate). Subsequently the mixture was heated under reflux at boiling for a further 2 hours.

Then the mixture was cooled and poured on a mixture of 2 kg of ice and 500 grams of glacial acetic acid. The suspension obtained was extracted with toluene. The extract was dried with sodium sulfate and evaporated in vacuo. The oily residue was distilled in a high vacuum. 1-Methylcyclopropyl-bis-(4-chlorophenyl)-carbinol=(bis-(p-chlorophenyl)-1-methylcyclopropyl-methanol) distilled at B.P.$_{0.9\ mm}$ 180°–182° C.

Amount: 822.8 grams=67% of theory Yellow Oil.

Analysis: $C_{17}H_{16}Cl_2O$ (Mol. Wt. 307), Calculated: C 66.4, H 5.2, Cl 23.1, Found: 66.2, 5.1, 23.0.

EXAMPLE 2

70 grams of 1-fluoro-4-bromobenzene were dissolved in 300 ml of diethylether and there was produced therefrom the corresponding Grignard compound with 9.6 grams of magnesium shavings. There was dropped into this solution under reflux 26.9 grams of ethyl 1-methylcyclopropylcarboxylate. The mixture was stirred subsequently for a further 2 hours. The mixture was poured on ice and neutralized with dilute hydrochloric acid. The ether containing solution was evaporated. There remained behind a light brown oil which was distilled in a vacuum. At B.P.$_1$ 141°–143° C. there distilled an almost colorless oil.

Amount: 38.5 grams, corresponding to 70.25% of Theory, α-(1-Methylcyclopropyl)-4,4′-difluorobenzhydrol.

Analysis: $C_{17}H_{16}OF_2$ (Mol. Wt. 274), Calculated: C 74.5, H 5.8, F 13.8, Found: 74.2, 5.7, 13.6.

EXAMPLE 3

94.9 grams of 1,4-dibromobenzene were dissolved in 400 ml of diethyl ether and there was produced the corresponding Grignard compound therefrom with 9.6 grams of magnesium shavings. This solution was subsequently reacted with 26.9 grams of ethyl 1-methylcyclopropylcarboxylate at about 30° C. and subsequently worked up as described in Example 2. The thus obtained light red oil was distilled in a vacuum at B.P.$_{0.5}$ 187°–189° C.

Amount: 45.8 grams, corresponding to 58.1% of Theory α-(1-Methylcyclopropyl)-4,4'-dibromobenzhydrol.

Analysis: $C_{17}H_{16}OBr_2$ (Mol. Wt. 394), Calculated: C 51.8, H 4.1, Br 40.6, 51.7, 4.0, 40.3.

The compounds of formula I can be used alone or together with suitable carriers and/or other additives. Suitable carriers and additives can be solid or liquid and correspond to the customary materials in the formulation art, as e.g. natural or regenerated mineral materials, solvents, dispersing agents, wetting agents, adhesives, thickeners, binders or fertilizers.

As carriers there can be used for example kaolin, talcum, Bolus albus, loess, chalk, limestone, attapulgus clay, dolomite, diatomaceous earth, precipitated silica, alkaline earth metal silicates, sodium and potassium aluminum silicate (feldspar and mica), calcium and magnesium oxide, fertilizers such as ammonium sulfate, ammonium phosphate, ammonium nitrate and urea, ground plant products such as ground grain, cottonseed hull meal, wood flour, nut sheet flour, powdered cellulose, activated carbon or mixtures.

As adhesives there can be used for example olein-lime mixture, cellulose derivatives (methyl cellulose, carboxymethyl cellulose). As wetting agents or tensides there can be used for example soaps, sulfonated fats, fatty acid esters and fatty alcohol sulfonates, quaternary ammonium compounds of relatively high molecular weight and non-ionic emulsifiers such as condensation products of fatty alcohols with ethylene oxide, e.g. with 5-20 ethylene oxide residues per molecule and 8-18 carbon atoms in the fatty alcohol portion (e.g. stearyl alcohol), hydroxyethylene glycol ethers of mono and dialkyl phenols with 5 to 20 ethylene oxide residues per molecule and 8-9 carbon atoms in the alkyl group of the phenol (e.g. p-nonyl phenol), alkali and alkaline earth metal salts of lignin sulfonic acid (e.g. sodium ligninsulfonate), polyethylene glycol, alkali metal salts of the alkyl and alkylaryl sulfonates, such as the sodium salt; alkyl sulfates; alkylamide sulfonates, including fatty methyl taurides; the alkylaryl polyether alcohols.

The content of active material in fungicidal compositions is between 0.1 and 99%, especially between 0.1 and 95%. The content of solid and/or liquid additives is 1 to 99.9%, preferably 5 to 99.9%. When a tenside is used its content is advantageously between 0.1–25%.

For application the compounds of formula (I) can be worked up in the following form for application (whereby the weight percentages given in parantheses represent preferred amount of material):

Solid forms for working up: dusts and strewing agent (up to 10%) granulates, encapsulated granulates, impregnated granulates and homogeneous granulates, pellets (granules) 1 to 80%.

Liquid forms for working up.
(a) Dispersible active material concentrates in water: wettable powders and pastes (25–90% in the commercial package, 0.01 to 15% in solution ready for use);
emulsions and solution concentrates (10 to 50%; 0.01 to 15% in solution ready for use)
(b) solutions (0.1 to 20%); aerosols.

The active material of formula (I) of the present invention for example can be formulated as follows:

Dusts

For the production of an (a) 5% and (b) 2% dust there are used the following materials:

| (a) | Active material | 5 parts |
|---|---|---|
|  | Talcum | 9 parts |
| (b) | Active material | 2 parts |
|  | Highly dispersed silica | 1 part |
|  | Talcum | 97 parts |

The active material is mixed with the carriers and ground and can be used in this form as a dust.

Granulate

For the production of a 5% granulate there are used the following materials:

| Active material | 5 parts |
|---|---|
| Epoxidized plant oil (e.g. epoxidized soybean oil) | 0.25 part |
| cetyl polyglycol ether | 0.25 parts |
| polyethylene glycol | 3.5 parts |
| Kaolin (particle size 0.3–0.8 mm) | 91 parts |

The active material is mixed with the epoxidized plant oil and dissolved in 6 parts of acetone, hereupon there are added polyethylene glycol and cetyl polyglycol ether. The thus obtained solution is sprayed on kaolin, and subsequently the acetone is evaporated in a vacuum. This type of microgranulate is used advantageously for combatting earth fungi.

Wettable Powder

For the production of an (a) 70%, (b) 40%, (c) and (d) 25% and (e) 10% wettable powder there are used the following components:

| (a) | Active material | 70 parts |
|---|---|---|
|  | sodium dibutylnaphthyl sulfonate | 5 parts |
|  | naphthalenesulfonic acid-phenolsulfonic acid-formaldehyde condensate 3:2:1 | 3 parts |
|  | Kaolin | 10 parts |
|  | Champagne chalk | 12 parts |
| (b) | Active material | 40 parts |
|  | sodium ligninsulfonate | 5 parts |
|  | sodium dibutylnaphthalenesulfonate | 1 part |
|  | silica | 54 parts |
| (c) | Active material | 25 parts |
|  | Calcium ligninsulfonate | 4.5 parts |
|  | Champagne chalk/hydroxyethyl cellulose mixture (1:1) | 1.9 parts |
|  | sodium dibutylnaphthalenesulfonate | 1.5 parts |
|  | silica | 19.5 parts |
|  | Champagne chalk | 19.5 parts |
|  | Kaolin | 28.1 parts |
| (d) | Active material | 25 parts |
|  | Isooctylphenoxy-polyoxyethylene ethanol | 2.5 parts |
|  | Champagne chalk/hydroxyethyl cellulose mixture (1:1) | 1.7 parts |
|  | sodium aluminum silicate | 8.3 parts |
|  | Kieselguhr | 16.5 parts |
|  | Kaolin | 46 parts |
| (e) | Active material | 10 parts |
|  | mixture of the sodium salt of saturated higher fatty alcohol sulfates | 3 parts |
|  | naphthalenesulfonic acid-formaldehyde condensate | 5 parts |
|  | Kaolin | 82 parts |

The active material is intensively mixed in suitable mixers with the additive materials and ground on corresponding mills and rolls. There are obtained wettable powders of advantageous wettability and suspensibility which are diluted with water to suspensions of the desired concentration and particularly permit use for application to leaves.

Emulsifiable Concentrates

The following materials are used to produce a 25% emulsifiable concentrate

| Active Material | 25 parts |
|---|---|
| Epoxidized plant oil | 2.5 parts |
| Alkylarylsulfonate/fatty alcohol-polyglycol ether mixture | 10 parts |
| dimethyl formamide | 5 parts |
| Xylene | 57.5 parts |

There can be produced from such concentrates by dilution with water emulsions of the desired concentration which are particularly suited for application to leaves.

It goes without saying that to broaden their spectrum of the activity the compounds of formula (I) adjusted to the given circumstances can be employed together with other suitable pesticides or plant growth promoting active materials. As the mixing partner there can be used, depending on the area of use, for example the active materials set forth in German OS No. 2506598 pages 6 to 12. The entire disclosure of the German OS is hereby incorporated by reference and relied upon. Thus there can be used for example elemental sulfur, ammonium polysulfide, barium polysulfide, sodium polysulfide, calcium polysulfide, calcium thiosulfate, calcium hypochlorite, boric acid, sodium tetraboride decahydrate (borax), zinc chloride, magnesium borate, nickel sulfate, potassium chromate, lead arsenate, cadmium chloride, cadmium carbonate, copper (I) oxide (Kupferox 10), Bordeaux liquor, copper (II) sulfate pentahydrate, fasic copper (II) chlroide, copper phosphate, tribasic copper (II) sulfate, basic copper (II) carbonate, copper (II)-dihydrazine sulfate, copper ammine complex, copper (II) sulfate-ammonium carbonate mixture, copper (II) chloride-basic copper (II) sulfate mixture, basic copper (II) carbonate-zinc salt mixture, copper (II)-zinc chromate complex, copper (II)-zinc-cadmium-calcium-chromate complex, copper (II) salt of oleic acid, copper (II) salts of fatty acids, e.g. stearic acid, copper (II) salt of naphthenic acid, copper (II) salt of 8-hydroxyquinoline, copper (II) salt of 1,2-naphtho-quinone oxime-(2), copper (II) salt of 3-phenylsalicylate, bis-(tri-n-butyltin) oxide, triphenyltin hydroxide, triphenyltin acetate, bis-(tributyltin) succinate, mercury (I) chloride (calomel), mercury (I) chloride, mercury (II) oxide, mercury-zinc chromate complex, mercury (II) acetate, ethyl mercury chloride, 2-hydroxyethyl mercury acetate, ethyl mercury isothiocyanate, 3-ethoxypropyl mercury bromide, chloromethoxypropyl mercury acetate, methoxyethyl mercury chloride, 2-methoxyethyl mercury silicate, bis-(methyl mercury) sulfate, bis-(methyl mercury) ammonium acetate, ethyl mercury acetate, 2-methoxyethyl mercury acetate, ethyl mercury phosphate, isopropylmethyl mercury acetate, methyl mercury cyanide, methyl mercury benzoate, N-cyano-N'-(methyl mercury) guanidine, methyl mercury pentachlorophenolate, ethyl mercury-2,3-dihydroxypropyl mercaptide, methyl mercury-8-hydroxyquinolate, N-(methyl mercury)-1,4,5,6,7-hexachlorobicyclo-[2.2.1]-hept-5-ene-2,3-dicarboximide, N-(ethyl mercury)-1,4,5,6,7-hexachlorobicyclo-[2.2.1]-hepten-2,3-dicarboximide, sodium salt of ethyl mercury thiosalicylate, N-(ethyl mercury)-p-toluenesulfonanilide, phenyl mercury acetate, phenyl mercury propionate, phenyl mercury triethanol ammonium acetate, phenyl mercury urea, N-(phenyl mercury)-1,4,5,6,7,7-hexachlorobicyclo-([2.2.1]) hept-5-en-2,3-dicarboximide, phenyl mercury dimethyl dithiocarbomate, phenyl mercury formamide, phenyl mercury chloride, phenyl mercury acetate, phenyl mercury benzoate, phenyl mercury borate, phenyl mercury hydroxide, phenyl mercury iodide, basic phenyl mercury nitrate, basic phenyl mercury monoethanol amine acetate, phenyl mercury salicylate, hydroxy mercury chlorophenol, hydroxy mercury trichlorophenol, hydroxy mercury nitrophenol, N-phenyl mercury ethylenediamine, phenyl mercury monoethanol ammonium acetate, pyridyl mercury acetate, diphenyl mercury-8-hydroxyquinolate, mercury (II) complex with organic phosphates, mixture of methyl mercury-2,3-dihydroxypropyl mercaptide and methyl mercury acetate, mixture of ethyl mercury-2,3-dihydroxypropyl-mercaptide and ethyl mercury acetate, mixture of hydroxy-mercury chlorophenol and hydroxymercury nitrophenol, mercury-cadmium-organic complexes, cadmium succinate, cadmium-di-n-propyl xanthogenate, cadmium-8-hydroxyquinolate, phenylamino cadmium acetate, phenylamino cadmium dilactate, methyl arsinosulfide, zinc octate, zinc oleate, formalin, paraformaldehyde, acrolein, methyl bromide, methyl isothiocyanate, tetraiodoethylene, 1,3-dichloropropylene and related chlorinated $C_3$-hydrocarbons, 1-chloro-3-bromopropene-(1), trans-1,4-dibromobutene-(2), 1,3-dichloropropene-(1), 1-chloro-2-nitropropane, 2-chloro-1-nitropropane trichloronitromethane, dichlorotetrafluoroacetone, sodium salt of propionic acid, calcium propionate, chlorofumaric acid-bis-$\beta$-chloroethyl ester, sorbic acid and its potassium salt, 2-propen-1,1-diol acetate, 2-aminobutane, dodecylguanidine acetate, dodecylguanidine phthalate, $\alpha$-chloroacetyl-1,3-aminopropionitrile, $\alpha$-bromoacetyl valinamide, 1,2-dichloro-1-(methylsulfonyl)-ethylene, 1,2-dichloro-1-(butylsulfonyl)-ethylene, trans-1,2-bis-(n-propylsulfonyl)-ethylene, p-dichlorobenzene, hexachlorobenzene, 1,2,4,5-tetrachloro-4-nitrobenzene, pentachloronitrobenzene, 1,3,5-trichloro-2,4,6-trinitrobenzene, isomeric mixture of 1,3,4-trichloro-2,6-dinitrobenzene and 1,2,3-trichloro-4,6-dinitrobenzene, 2,4,5,6-tetrachloroisophthalonitrile, 2,4-dinitrophenyl thiocyanide, diphenyl, o-nitrodiphenyl, 1-chloro-2,4-dinitronaphthalene, acenaphthene, 2,4,6-trichlorophenol, 2,4,5-trichlorophenol, 2,4,5-trichlorophenyl acetate, 2,4,5-trichlorophenyl chloroacetate, zinc salt of trichlorophenol, m-cresyl acetate, 2,3,4,6-tetrachlorophenol, pentachlorophenol, o-dihydroxybenzene, 2,4-dihydroxy-n-hexylbenzene, 2-phenylphenol, 3,5-dibromosalicylaldehyde, 2-benzyl-4-chlorophenol, 2,2'-dihydroxy-5,5'-dichlorodiphenyl methane, 2,2'-dihydroxy-3,3',5,5',6,6'-hexachlorodiphenylmethane, 2,2'-dihydroxy-5,5'-dichloro-diphenyl sulfide, 2,2'-dihydroxy-3,3',5,5'-tetrachloro-diphenyl sulfide, 2,2'-dihydroxy-3,3',5,5'-tetrachloro-diphenyl sulfide disodium salt, 4-chloro-o-phenylphenol, 1,4-dichloro-2,5-dimethoxybenzene, salicylanilide, bismuth salicylate, trifluoromethylsalicylanilide halogenated with chlorine or bromine, brominated salicylanilide, (3,5-dimethyl-4-chlorophenoxy)ethanol, 2-(1-methyl-n-propyl)-4,6-dinitrophenyl-2-methyl crotonate, 2-(1-methyl-n-propyl)-4,6-dinitrophenylisopropyl crotonate, 2-(1-methyl-n-heptyl)-4,6-dinitro-phenyl crotonate, methyl-2,6-dinitro-4(1-ethylhexyl)-phenylcarbonate plus methyl-3,6-dinitro-4-(1-propyl-pentyl) phenyl carbonate, 4-nonyl-2,6-dinitrophenyl butyrate, 5-methyl-2-(1-methyl-n-heptyl)-4,6-dinitro-phenyl thiocarbonate, 2,6-dichloro-4-nitroaniline, 2-cyanoethyl-N-phenyl carbamate, propynyl-N-phenyl carbamate, o-(2-bromoacetoxy)-acetanilide, 2,3,5,6-tetrachlorobenzoquinone (1,4), 2,3-dichloro-naphthoquinone (1,4), 2-chloro-3-acetamino-naphthoquinone (1,4), 4-methyl-2,3,5,10-tetrahydro-3,5,10-trioxo-4H4-H-naphtho(1,3,-b)-1,4-triazine, 2,3,6,7-tetrachloro-4a,8a-epoxy-1,2,3,4,4a,8a-hexahydro-1,4-methanonaphthalene,5,8-dione, quinoximobenzoyl hydrazone, N-(trichloromethylthio) phthalimide, N-(trichloromethylthio) cyclohex-4-en-1,2-dicarboximide, N-(1,1,2,2-tetrachloroethylthio) cyclohex-4-en-1,2-dicarboximide, N-methanesulfonyl-N-trichloroethylthio-p-chloroaniline, N'-dichlorofluoromethylthio-N-dimethyl-N'-phenylsulfamide,5-(2-pyridyl-1-oxide)-S'-trichloromethyldisulfide, O,O,O-trimethyl thiophosphate, O,O-diethyl-phthalimido phosphonothioate, 5-amino-bis-(dimethylamido) phosphinyl-3-phenyl-1,2,4-triazole, 5-methylamino-bis-(dimethylamido) phosphinyl-3-phenyl-1,2,4-triazole, O,O-diethyl-O-2-pyrazinyl phosphorothioate, O-ethyl-S,S-diphenyldithiophosphate, O-ethyl-S-benzyl phenyl dithiophosphonate, O,O-diethyl-S-benzylthiophosphate, zinc salt of dithiocarbazinic acid, sodium-N-methyl dithiocarbamate, sodium-N-methoxyethyl dithiocarbamate, sodium N,N-diethyl dithiocarbamate, ammonium N,N-dimethyl dithiocarbamate, zinc N,N-dimethyl dithiocarbamte, iron-N,N-dimethyl dithiocarbamate, copper-N,N-dimethyl dithiocarbamate, disodium ethylene-1,2-bis dithiocarbamate, zinc-ethylene-1,2-bis-dithiocarbamate, iron ethylene-1,2-bis dithiocarbamate, manganese (II)-ethylene-1,2-bis-dithiocarbamate, calcium-ethylene-1,2-bis-dithiocarbamate, ammonium-ethylene-1,2-bis-dithiocarbamate, zinc-propylene-1,2-bis dithiocarbamate, bis (dimethylthiocarbamyl)-ethylene-1,2-bis-dithiocarbamate, complex consisting of manganese (II)-ethylene-1,2-bis-dithiocarbamate and Mancozeb, tetraethylthiuram monosulfide, bis-(N,N-dimethyl-dithiocarbamyl mercapto)-methylarsine, tetramethylthuiram disulfide, bipyrridyl thiuramdisulfide, N,N'-bis-(dimethylamino)-thuiram disulfide, polyethylene thiuramdisulfide, complex consisting of zinc ethylene-1,2-bis-dithio-carbamate and polyethylene thiuramdisulfide, bis-(3,4-dichloro-2(5)-furanoyl) ether (mucochleric anhydride), 2-methoxymethyl-5-nitrofurane, 5-nitrofurfuraldoxime, 5-nitro-furfuryl amidoxime, 1-hydroxy-3-acetyl-6-methyl-cyclohexen-(5)-dione-(2,4) (dehydroacetic acid), 3-[-3,5-dimethyl-2-hydroxycyclohexyl)-2-hydroxyethyl]-glutarimid(cycloheximido) phthalimide, pyridin-2-thiol-1-oxide or 1-hydroxypyridine-2-thione, zinc salt of pyridine-2-thiol-1-oxide, manganese (II) salt of pyridine-2-thiol-1-oxide, S-1(1-oxido-2-pyridyl) isothiuronium chloride, α,α-bis(4-chlorophenyl)-3-pyridine methanol, 8-hydroxyquinoline, 8-hydroxyquinoline sulfate, benzoyl-8-hydroxyquinoline salicylate, 3-(2-methylpiperidino)propyl-3,4-dichloro-benzoate, 6-ethoxy-1,2-dihydro-2,2,4-methylquinoline, N-lauryl isoquinolium bromide, 9-(p-n-hexyloxyphenyl)-10-methyl-acridinium chloride, 9-(p-n-hexyloxyphenyl)-10-methyl acridinium-p-toluenesulfonate, 2-n-heptadecylimidazolidine acetate, 1-hydroxyethyl-2-heptadecylimidazolidine, 1-phenyl-3,5-dimethyl-4-nitrosopyrazole, 1-p-chlorophenyl-3,5-dimethyl-4-nitrosopyrazole, 1-p-sulfacylphenyl-3,5-dimethyl-4-nitrosopyrazole, N-(1-phenyl-2-nitropropyl) piperazine, 2-dimethylamino-5-methyl-5-n-butyl-4-hydroxy-pyrimidine, N-dodecyl-1,4,5,6-tetrahydropyrimidine, N-dodecyl-2-methyl-1,4,5,6-tetrahydropyrimidine, 2-n-heptadecyltetrahydropyrimidine, 1-(4-amino-4-propyl-5-pyrimidyl-methyl)-2-methyl pyridinium chloride hydroxy chloride, 2-(2'-furyl)-benzimidazole, 3-dodecyl-1-methyl-2-phenylbenzimidazolium-ferricyanide, methyl-N-benzimidazol-2-yl-N-(butylcarbamoyl) carbamate, 2-(o-chloroanilino)-4,6-dichloro-sym.triazine, 2-ethylamino-6-methyl-5-n-butyl-4-hydroxy pyrimidine, 5-chloro-4-phenyl-1,2-dithiol-3-one, 2,3-dicyano-1,4-dithiaanthraquinone, 2-(4-thiazolyl)-benzimidazole, 4-(2-chlorophenylhydrazono)-3-methyl-5-isoxazolone, thiazolidinen-4-thione-(2), 3-(p-chlorophenyl)-5-methylrhodanine, 3,5-dimethyltetrahydro-1,3,5-thiadiazin-2-thione, 3,3'-ethylene-bis-(tetrahydro-4,6-dimethyl)-2H-1,3,5-thiadiazin-2-thione),3-benzylidenamino-4-phenylthiazolin-7-thione, zinc salt of 6-chlorobenzothiazol-2-thiol, 6-α-diethylamino-ethoxy-2-dimethylamino-benzothiazole dihydrochloride, monoethanolammoniumbenzothiazole-2-thiol, lauryl pyridinium-5-chloro-2-mercaptobenzothiazole, zinc and sodium salts of 2-mercaptobenzothiazole and dimethylcarbamate, 6-(diethylaminoethoxy)-2-dimethylaminobenzothiazole dihydrochloride, 3-trichloromethylthiobenzothiazolone, 3-trichloromethylthiobenzoxazolone, 3-(trichloromethyl)-5-ethoxy-1,2,4-thiadiazol, 6-methyl-2-oxo-1,3-dithiolo[4,5-b]-quinoxaline, 2-thio-1,3-dithiolo[4,5-b]-quinoxaline, 2,3-dihydro-5-carboxanilido-6-methyl-1,4-oxathine, 3,3,4,4-tetrachlorotetrahydrothiophen-1,1-dioxide, 2,3-dihydro-5-carboxanilido-6-methyl-1,4-oxathin-4,4-dioxide, ethyl trimethylammonium bromide, n-alkyl($C_{12}$,$C_{14}$,$C_{16}$) dimethylbenzylammonium chloride, alkenyl dimethyl ethyl ammonium bromide, dialkyldimethylammoniumbromide, alkyl-dimethylbenzylammonium chloride, alkyl $C_9$-$C_{15}$ tolylmethyl trimethylammonium chloride, di-isobutyl-cresoxyethoxyethyldimethylbenzylammonium chloride, p-di-isobutylphenoxyethoxyethyl dimethylammonium chloride, benzoyltrimethyl ammonium bromide, gliotoxin, 2,4-diguanido-3,5,6-trihydroxy-cyclohexyl 5-deoxy-2-O-(2-deoxy-2-methylamino-α-L-glucopyranosyl)-3-C-formyl-3-L-lyxopentofuranoside (streptomycin), 7-chloro-4,6-dimethoxycumaran-3-one-2-spiro-1'-(2'-methoxy-6'-methylcyclohex-2'-en-4'-one) Griseofulvin), 4-dimethylamino-1,4,4a,5,5a6,11,12-octahydro-3,5,6,10,12,12a-hexahydroxy-6-methyl-1,11-dioxo-2-naphthacencarboximide (Oxytetracyclin), 7-chloro-4-dimethylamine-1,4,4a,5,5a,6,11,12-octahydro-3,6,10,12,12 pentahydroxy-6-methyl-1,11-dioxo-2-naphthacencarboximide (Chlorotetracyclin), Pimaricin, Lanomycin, Phleomycin, Kasugamycin, Phytoactin, D(−)-threo-2,2-dichloro-N-[3-hydroxy-α-(hydroxymethyl)-17-p-nitrophenethyl]9 acetamide, Blasticidiin-S-benzylamino-benzenesulfonate, N-(3-nitrophenyl) itaconimide, phenoxyacetic acid, sodium-p-dimethylaminobenzenediazo sulfonate, acrolein phenylhydrazone, 2-chloroacetaldehyde (2,4-dinitrophenyl)-hydrazone, 2-chloro-3-(tolylsulfonyl)-propionitrile, 1-chloro-2-phenylpentan-diol (4,5)-thione-(3), p-nonyl-phenoxypolyethylenoxyethanol-iodide complex, (α-nitromethyl)-o-chlorobenzylthioethylamine hydrochloride, 3-(p.t.-butylphenylsulfonyl) acrylonitrile, octachlorocyclohexenone, pentachlorobenzyl alcohol, pentachlorobenzyl acetate, pentachlorobenzaldehyde cyanohydrin, 2-norcamphane methanol, 2,6-bis-(dimethylaminomethyl)-cyclohexanone, decachlorooctahydro-1,3,4-methano-2H-cyclobuta[cd] pentalen-2-one, 1-(3-chloroallyl)-3,5,7-triaza-1-azonia adamantane hydrochloride, coal tar and high oven tar, mixture of nickel sulfate-Maneb, mixture of Maneb-mercaptobenzothiazole, mixture of Zineb-mercaptobenzothiazole, mixture of Zineb-nickel (II) chloride, mixture of Zineb-nickel (II) sulfate, mixture of Ziran-basic copper sulfate, mixture of Ziran-zinc-mercaptobenzothiazole, mixture of Thiram-cadmium chloride hydrate, mixture of Thiram-hydroxymercury chlorophenol, mixture of Thiram-phenyl mercury acetate, mixture of polyethylene-bis-thiramsulfide-copper oxychloride, mixture of methylarsine-bis-(dimethyldithiocarbamate)-Ziram-Thiram, mixture of Folpet-phenylmercuryacetate, mixture of Dodine-Farbam-sulfur, mixture of Dithianone-copper oxychloride, mixture of Dichlone-Farbam-sulfur, mixture of Dinocap-dinitrooctylphenol, mixture of Captan-quintozene-tribasic copper sulfate, mixture of cadmium propionate-phenyl mercury propionate, formaldehyde-urea mixture, mixture of phenylammonium cadmium dilactate-phenyl mercury formamide, and mixture of basic copper sulfate-zinc salt.

EXAMPLE 4

Action Against *Piricularia Oryzae* On Rice

Rice plants after two weeks cultivation were sprayed with a liquor (0.02% active material) made from a wettable powder of the active material. After 48 hours the treated plants were infected with a konidium suspension of the fungi. After 5 days incubation at 95–100% relative humidity and 24° C. the attack of the fungi was evaluated.

The compound α-(1-methylcyclopropyl)-4,4'-dichlorobenzhydrol showed a very strong plant fungicide activity. At most the attack of the fungi on the treated plants was 0–5% which corresponds to an effective activity of 95–100%.

For comparison in an entirely analogous manner there was used as the active material the compound di-(p-chlorophenyl)-cyclopropylmethanol. It merely showed an unsatisfactory partial activity, i.e. the average attack on the fungi was in the range of 20–50%.

The entire disclosure of German priority application No. P 3206225.7 is hereby incorporated by reference.

What is claimed is:

1. A benzhydrol derivative of formula (I)

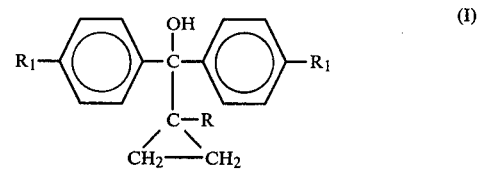

in which R is ethyl or methyl and $R_1$ is halogen or hydrogen.

2. A benzhydrol derivative according to claim 1 where $R_1$ is hydrogen.

3. A benzhydrol derivative according to claim 1 where $R_1$ is chlorine, bromine or fluorine.

4. A benzhydrol derivative according to claim 1 wherein $R_1$ is fluorine or chlorine and R is methyl.

5. A benzhydrol derivative according to claim 1 which is α-(1-methylcyclopropyl)-4,4'-dichlorobenzhydrol.

6. A fungicidal composition comprising a fungicidally effective amount of a compound according to claim 1 together with at least one member of the group consisting of carriers and surface active agents.

7. A method of combatting fungi or preventing the attack of fungi comprising applying to the habitat of the fungi a fungicidally effect amount of a compound according to claim 1.

8. A method according to claim 7 wherein the compound is α-(1-methylcyclopropyl)-4,4'-dichlorobenzhydrol.

9. A method according to claim 7 wherein the fungi are plant pathogenic fungi and the compound is applied to the plants or their surrounding soil.

10. A method according to claim 9 wherein the compound is α-(1-methylcyclopropyl)-4,4'-dichlorobenzhydrol.

11. A method according to claim 9 wherein the compound is applied to the leaves.

12. A method according to claim 9 wherein the plants are rice plants.

13. A method according to claim 12 wherein the compound is α-(1-methylcyclopropyl)-4,4'-dichlorobenzhydrol.

14. A method according to claim 12 wherein the fungi are *Piricularia oryzae*.

15. A method according to claim 14 wherein the compound is α-(1-methylcyclopropyl)-4,4'-dichlorobenzhydrol.

* * * * *